United States Patent [19]

Dean et al.

[11] 4,249,526
[45] Feb. 10, 1981

[54] INHALATION DEVICE

[75] Inventors: Desmond A. Dean, Beeston; David M. Young, Loughborough, both of England

[73] Assignee: Fisons Limited, London, England

[21] Appl. No.: 29,318

[22] Filed: Apr. 12, 1979

[30] Foreign Application Priority Data

May 3, 1978 [GB] United Kingdom .............. 17418/78

[51] Int. Cl.³ ............................................. A61M 15/06
[52] U.S. Cl. ................................................ 128/203.15
[58] Field of Search ..................................... 128/203.15

[56] References Cited

U.S. PATENT DOCUMENTS 2,587,215  2/1952  Priestly ........................... 128/203.15
3,807,400  4/1974  Cocozza .......................... 128/203.15

Primary Examiner—Henry J. Recla
Attorney, Agent, or Firm—Merriam, Marshall & Bicknell

[57] ABSTRACT

An inhalation device for powdered medicaments in which the opening of the container in which the medicament is initially contained is achieved simply and reliably in situ in the device, the device being provided with means (24) for locating the container in a position to be opened and with appropriate opening means (20, 21) for the container, said opening means being normally in a non-opening position but movable successively into and out of a container opening position by movement in one direction of a cam surface (7, 8, 30, 31) acting thereon, the cam surface being provided with a step or steps (9, 10) to prevent reverse movement of the cam surface after opening of the container has been achieved. The cam surface (7, 8) is preferably provided on one housing member (1) and the opening means (20, 21) on a second housing member (2) so that attachment of the housing members (1, 2) simultaneously opens the container.

5 Claims, 7 Drawing Figures

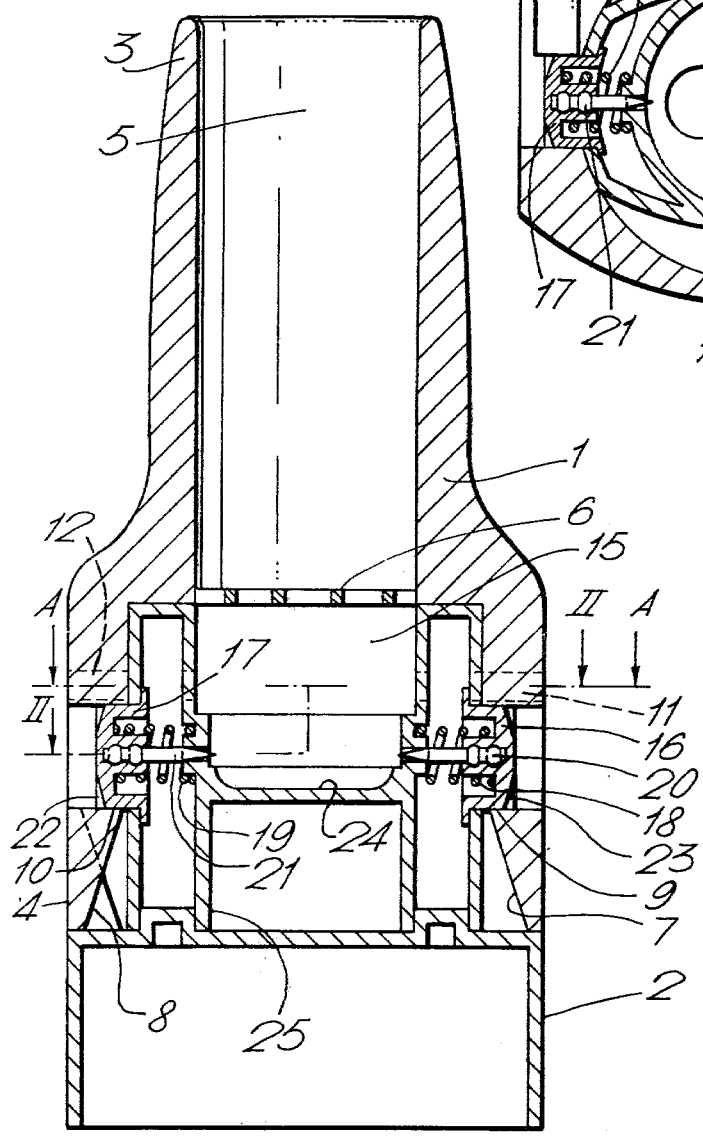

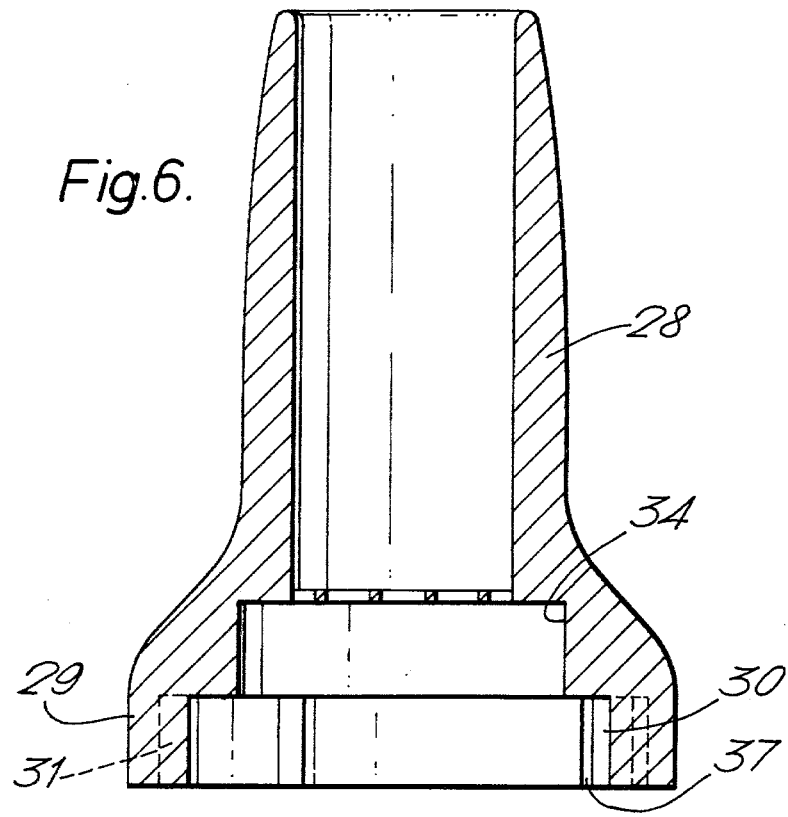
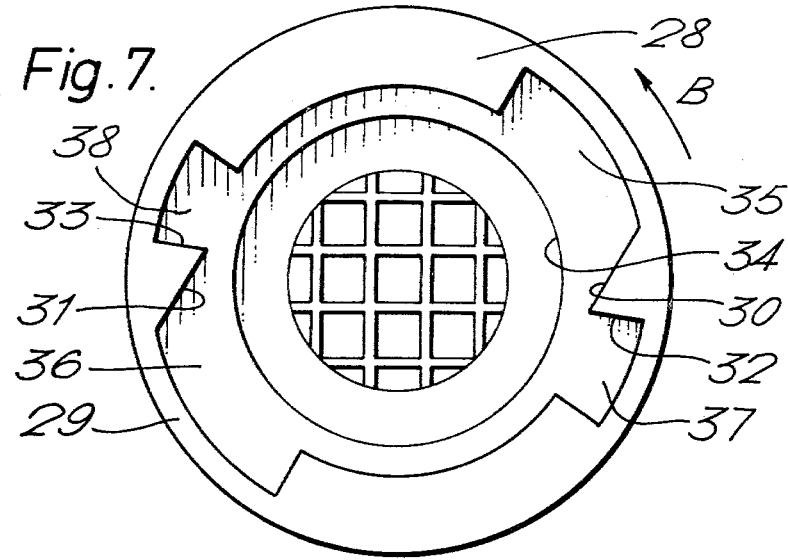

INHALATION DEVICE

This invention concerns improvements in or relating to inhalation devices for powdered medicaments.

Many inhalation devices are known in which a medicament powder contained initially in a container, e.g. a gelatin capsule, is administered to the patient by first opening the container and then entraining the powder in an airstream which is then inhaled. The opening of the container and the subsequent entrainment of the powder may be achieved in a variety of ways. For example, the container may be pierced by pins which are then retracted, and the container is rotated and/or vibrated in the airstream to expel the powder through the pierced holes. Devices of this type are described in U.K. Pat. No. 1,122,284. Alternatively, the container may be physically separated into two or more parts, for example by cutting or by pulling two separate portions thereof apart, as in the case of a gelatin capsule. In the case of such devices, it is not of course essential to rotate or vibrate the container subsequently to expel the powder into the airstream.

This invention has as its object inhalation devices wherein the opening of the container is achieved in a simple and effective manner in situ in the device, the term 'opening' being used herein to include any means of allowing egress of the powder, e.g. piercing or cutting the container or pulling it apart.

Accordingly, this invention provides an inhalation device for powdered medicaments contained initially in a container, which device is provided with means for locating the container in a position to be opened and appropriate opening means for the container, said opening means being normally in a non-opening position but movable successively into and out of a container opening position by movement in one direction of a cam surface acting thereon, said cam surface being provided with a step or steps to prevent reverse movement thereof when the opening means is in a non-opening position after passing through a container opening position.

The means for locating the container in a position to be opened may be any such means appropriate to the form of container employed. Thus for example, in the case of a gelatin capsule the means may take the form of a cup-like device, conveniently attached to a propeller-like member for rotating the capsule, which is designed and dimensioned so as to hold and retain one end of the capsule therein whilst the free portion thereof is cut, pierced, or detached therefrom. Alternatively, the container may be located in a suitably shaped depression in the device, wherein it is retained during cutting or piercing either by gravity or a further member provided for that purpose.

The opening means may be any appropriate to the container to be opened. Thus, for cutting, it may comprise one or more blades adapted to cut completely or partly across the container, whereas for piercing it may for example comprise one or more pins, for example, stainless steel pins sharpened either to a conventional conical point or, more preferably, sharpened by cutting a plane face across the pin at an angle to the axis thereof. For pulling the container apart, it may, where the locating means comprises a cup-like device, comprise a similar cup-like device for the free end of the container, the two devices being adapted to separate when the cam surface acts thereon.

Where the container is in the form of a conventional elongate capsule, e.g. of gelatin, it may most conveniently be pierced either through the centres of the crowns of the capsule or at a number of points, preferably two, symmetrically disposed around the shoulder at one end of the capsule. Naturally, when other containers are employed, the piercing means should be constructed and arranged appropriately.

The opening means for the container is preferably biassed away from the container and is moved into the container opening position against the bias and out of the container opening position under the influence of the bias. The bias is preferably provided by a spring member acting on the opening means.

Movement of the cam surface is preferably limited, for example by the provision of a stop member, so that the full movement thereof causes only a single operation of the opening means. By employing a construction of this type, it is ensured that, since the cam surface is prevented from reverse movement by the step or steps provided therein, no more than one hole can be pierced or more than one cut made in the container. In corresponding devices in which the cam surface is not prevented from reverse movement, if the movement of the cam surface is reversed the container may tend to shift slightly before piercing or cutting occurs again thereby tending to give two holes or cuts very close together. Under such conditions, shattering of the container, especially when in the form of a conventional gelatin capsule, may often occur, with the consequence that particles of the container may be inhaled by the patient.

The present invention is particularly applicable to devices such as those described and claimed in our British Pat. No. 1,122,284, and modifications thereof. In that Patent there are described devices for the oral inhalation of powdered medicaments in finely-divided form, which comprise a hollow elongate housing having at both ends thereof one or more passageways to permit the passage of air therethrough and having one end thereof adapted for insertion into the mouth. A propeller-like member is provided rotatably mounted in the housing on a rigid shaft coaxial with the longitudinal axis of the housing, and on the end of the propeller-like member furthest from the end of the housing adapted for insertion into the mouth, mounting means are provided adapted to receive and retain the container of the finely-divided medicament. A notable modification of such devices to which the present invention is also applicable consists in the replacement of the propeller-like member by tangential air inlets into a swirl chamber to cause the container to rotate. When such devices are provided with opening means as described hereinbefore, the cam surface to act thereon may be arranged to operate in a number of ways. Thus, for example, the cam surface may be provided on the inner surface of an annular member extending around the periphery of the device, angular displacement of which member causes operation of the opening means.

Alternatively and preferably, the device may comprise two housing members (as is convenient to allow insertion of medicament containers) which are attachable one to the other by relative longitudinal movement therebetween, and the cam surface may be arranged on the housing member not carrying the opening means such that the said relative longitudinal movement between the two housing members causes operation of the opening means. In this latter case, since reverse movement of the cam surface is prevented by the step or steps therein, the two members are retained in engagement upon said longitudinal movement. Thus, the action of engaging the two members simultaneously causes opening of the container. This is a very important advantage since it minimizes faulty use of the device, e.g. by preventing failure to open the container which frequently occurs due for example to forgetfulness in devices not having this feature. It is desirable, however, if the housing members are to be separated and thus the device is to be reusable for there to be provided a means for avoiding the step or steps in the cam surface. This means may conveniently take the form of a channel circumferentially spaced from the cam surface wherein that portion of the opening means which contacts the cam surface may slide. On relative rotation of the housing members, the step or steps in the cam surface may thus be avoided and the two housing members may be separated. Preferably the base of the channel is arranged such that separation of the two housing members requires the opening means to reciprocate against the bias so that the separation requires a positive pulling action to be applied thereto such as would not occur accidentally. Preferably the base of the channel is provided with a step or steps to prevent attachment of the two housing members by means of said channel.

Desirably, the housing members have the same cross-section in the region where they meet, which is of a low degree of symmetry, preferably having at most a 2-fold axis of symmetry, so that correct orientation of the housing members for connecting them together is indicated by an alignment of the cross-sections thereof. A particularly preferred cross-section is an ellipse.

If desired, the device may be provided with a means for indicating when a satisfactory air flow rate therethrough is achieved by the patient e.g. a whistle.

The invention will now be described, though only by way of illustration, with reference to the accompanying drawings, in which:

FIG. 1 is a longitudinal cross-section through a device of present invention;

FIG. 2 is a transverse cross-section through the device of FIG. 1 along the line II—II;

FIG. 6 is a longitudinal cross-section through the upper housing member of a second device of this invention; and FIG. 7 is a bottom plan view of the housing member of FIG. 6.

Similar parts in each of the figures are denoted by the same reference numeral.

Figure 3:
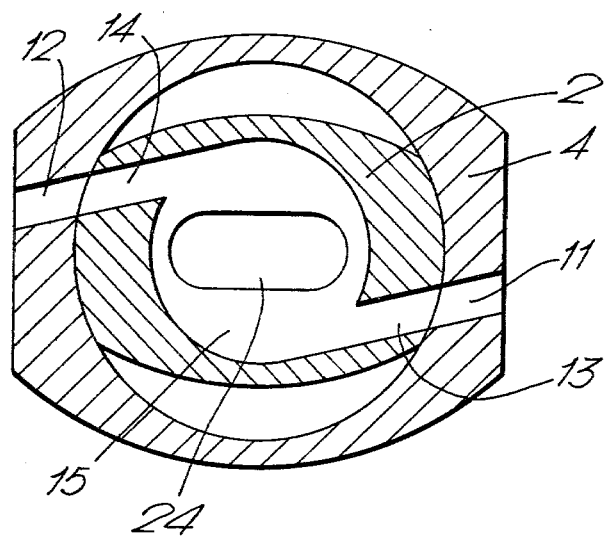
FIGS. 3 and 4 are transverse cross-sections through the device of FIG. 1 along the line A—A, respectively showing the orientation of the housing members when the device is in use and when about to be dismantled.

The device of FIGS. 1 to 4 is an inhalation device for medicaments provided in finely-divided form in gelatin capsules, and comprises an upper housing member 1 and a lower housing member 2 adapted to engage therewith. The upper housing member 1 is generally cylindrical at its upper end 3 and generally elliptical in cross-section at its lower end 4. Extending through upper housing member 1 is an air passageway 5, which is interrupted by a coarse sieve 6. Upper end 3 of housing member 1 is adapted for insertion into the mouth, and cam surfaces 7 and 8 are provided at the lower end 4, which cam surfaces are stepped at 9 and 10. Above the steps 9 and 10 are provided air inlets 11 and 12 which in use (see FIG. 3) communicate with passageways 13 and 14 through lower housing member 2 and enter swirl chamber 15 tangentially.

Below the inlets 11 and 12, there are located push buttons 16 and 17 attached to lower housing member 2 which are spring-biassed outwardly by springs 18 and 19 and which have fixedly mounted therein piercing pins 20 and 21. The push buttons 16 and 17 rest in apertures 22 and 23 in upper housing member 1.

A depression 24 is provided in a support member 25 fixedly attached to lower housing member 2, which depression is shaped and dimensioned so as to receive a conventional elongate gelatin capsule containing a medicament for inhalation.

In use, housing member 1 is detached, as will be described hereinafter, from housing member 2, and a capsule is placed in depression 24. In position, the crowns of the capsule register with the piercing pins 20 and 21. Then upper housing member 1 is appropriately located on lower housing member 2 and is pressed longitudinally thereonto. In so doing, push buttons 16 and 17 are depressed against the bias of springs 18 and 19 by cam surfaces 7 and 8, and piercing pins 20 and 21 pierce the crowns of the capsule. On further pressure, push buttons 16 and 17 ride over steps 9 and 10 and, by virtue of the spring bias acting thereon, return to the nonpiercing position shown in FIG. 1, thereby retaining housing member 1 in position on housing member 2. Mouthpiece 3 is then placed in the mouth and air is sucked through passageway 5. The air enters the housing through inlets 11 and 12 and passes into swirl chamber 15, dislodging the capsule from depression 24 and causing it to rotate about its 2-fold axis of symmetry. This movement causes the medicament to escape through the holes pierced in the crowns of the capsule and become entrained in the airstream to be carried into the mouth. The capsule is constrained within swirl chamber 15 by sieve 6.

Figure 4:
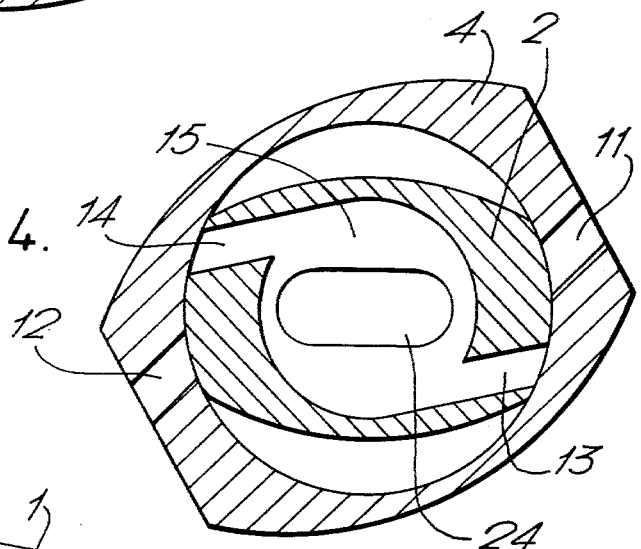

FIGS. 2, 3 and 4 show more clearly the relative dispositions of the inlets 11 and 12 and passageways 13 and 14 in the device of FIG. 1. In FIG. 3, the device is shown in its operative mode with the inlets 11 and 12 communicating with passageways 13 and 14, whereas in FIG. 4 the device is shown with the lower housing member 2 having been rotated with respect to the upper housing member 1 prior to pulling the two housing members apart. In this position there is no communication between the inlets and passageways, and thus no air can be inhaled through the device.

Figure 5:
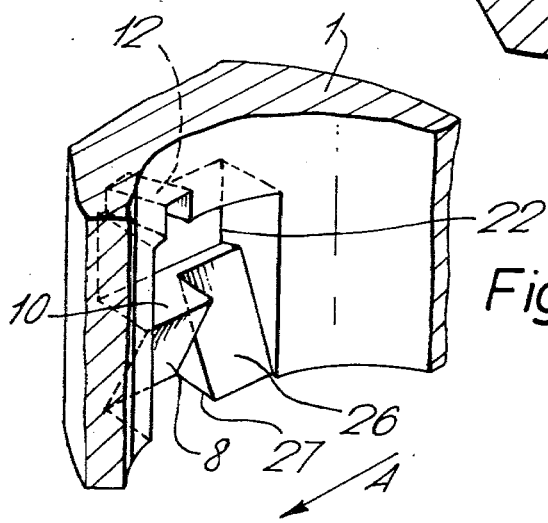
FIG. 5 is a perspective view of the cam surface arrangement employed in the device of FIGS. 1 to 4.

FIG. 5 shows the cam surface arrangement employed in the device of FIGS. 1 to 4. Cam surface 8 and step 10 operate as described in connection with FIG. 1, push button 17 resting, in the position shown in FIG. 1, above step 10 in aperture 22. After use, the upper housing member 1 is disengaged from the lower housing member 2 by movement of upper housing member 1 relative thereto, and to the push button 17, in the direction of arrow A such that push button 17 moves within aperture 22 until it rests above cam surface 26 which is inclined at an angle to cam surface 8. Upper housing member 1 can then be withdrawn from lower housing member 2 by pulling them apart such that push button 17 is caused to ride over cam surface 26 and finally over step 27 to prevent reassembly except by push button 17 riding over cam surface 8.

When push button 17 rests above cam surface 8, the inlet 12 communicates with swirl chamber 15 through corresponding passageway 14 through lower housing member 2. The passageways are so arranged however that when push button 17 rests above cam surface 26 there is no such communication.

FIGS. 6 and 7 show a second form of upper housing member which may be employed with the lower housing member 2 of FIG. 1 respectively in longitudinal cross-section and bottom plan views.

Upper housing member 28 in this embodiment is circular in cross-section and is provided with an annular rim 29 which carries cam surfaces 30 and 31 and associated steps 32 and 33. In use, the lower housing member 2 of FIG. 1 is located in upper housing member 28 and is retained therein by frictional contact around ridge 34. Push buttons 16 and 17 are located in use within recesses 35 and 36 in housing member 28 and housing member 28 is then rotated relative to lower housing member 2 in the direction of arrow B to cause the push buttons 16 and 17 to ride over cam surfaces 30 and 31, thereby causing the capsule to be pierced. The push buttons 16 and 17 thereafter spring under their bias over steps 32 and 33 into recesses 37 and 38, which prevents further movement of housing member 28 in either direction. After inhalation of the medicament, the two housing members are pulled longitudinally apart.

We claim:

1. An inhalation device for powdered medicaments contained initially in a container, which device comprises first and second housing members attachable one to the other by relative longitudinal movement therebetween to form a body defining an air flow path from an air flow inlet provided therein to an air outlet provided therein, means for locating the container in the air flow path in a position to be opened, appropriate opening means for the container provided on one of said housing members, a cam surface provided on the other of said housing members and adapted to act on the opening means, said opening means being normally in a non-container opening position but movable successively into and out of a container opening position by the action of the cam surface thereon occasioned by the longitudinal movement between the housing members, the cam surface including a step or steps to prevent reverse movement thereof when the opening means is in the non-container opening position after passing through the container opening position.

2. An inhalation device according to claim 1 wherein means are provided whereby the step or steps in the cam surface may be avoided and the two housing members may be separated.

3. An inhalation device according to claim 2 wherein said means comprise a channel circumferentially spaced from the cam surface wherein that portion of the opening means which contacts the cam surface may slide.

4. An inhalation device according to claim 3 wherein the base of the channel is arranged such that the opening means are caused thereby to reciprocate against the bias when the two housing members are separated.

5. An inhalation device according to claim 4 wherein the base of the channel is also provided with step or steps to prevent attachment of the two housing members by means of said channel.

* * * * *